(12) United States Patent
Pallucca et al.

(10) Patent No.: US 6,723,875 B1
(45) Date of Patent: Apr. 20, 2004

(54) PROCESS TO PREPARE ALKYL-UREAS FROM O,S-DIMETHYL DITHIOCARBONATE

(75) Inventors: Edoardo Pallucca, Settimo Milanese (IT); Jacopo Degani, Turin (IT); Anna Maria Serri, Milan (IT); Rita Fochi, Turin (IT); Sonia Gazzetto, Turin (IT); Claudia Fenoglio, Turin (IT); Claudio Ornati, Milan (IT); Mara Migliaccio, Turin (IT); Silvano Cadamuro, Turin (IT); Gianni Carvoli, Novara (IT)

(73) Assignee: Oxon Italia S.p.A., Milan (IT)

( * ) Notice: Subject to any disclaimer, the term of this patent is extended or adjusted under 35 U.S.C. 154(b) by 0 days.

(21) Appl. No.: 10/359,121

(22) Filed: Feb. 6, 2003

(51) Int. Cl.$^7$ ............................................. C07C 273/00
(52) U.S. Cl. ............................. 564/61; 564/57; 564/56
(58) Field of Search ............................. 564/32, 56, 57, 564/58, 61

(56) References Cited

U.S. PATENT DOCUMENTS

| | | | | |
|---|---|---|---|---|
| 4,725,680 A | * | 2/1988 | Barcelo et al. | 540/608 |
| 4,857,556 A | * | 8/1989 | Yamada et al. | 514/585 |
| 5,030,738 A | * | 7/1991 | Reiner | 549/535 |
| 5,925,762 A | * | 7/1999 | Thavonekham | 546/269.7 |

OTHER PUBLICATIONS

CA:96:20026 abs of Journal of Heterocyclic Chem. by Reynaud et al 17(8) pp 1789–92 1980.*
CA:129:54570 abs of Tetrahedron Letters by Anbazhagan et al 39(21) pp 3609–12 1998.*
CA:133:30563 abs of Synthetic Commun. by Mizuno et al 30(9) pp 1675–1688 2000.*
CA:120:30455 abs of Tetrahedron 49(34) by Tandel et al pp 7479–86 1993.*
Sagun K. Tandel et al., "Conversion of Thiocarbamates to Carbamates," Tetrahedron, V. 49, 1993, pp. 7479–7486.
Man–kit Leung et al., "S,S–Dimethyl Dithiocarbonate: A Convenient Reagant for the Synthesis of Symmetrical and Unsymmetrical Ureas," J. Org. Chem., V. 61, 1996, pp. 4175–4179.

* cited by examiner

*Primary Examiner*—Jean F. Vollano
(74) *Attorney, Agent, or Firm*—Young & Thompson

(57) ABSTRACT

The present invention relates to the preparation of alkyl-ureas, starting from O,S-dimethyl dithiocarbonate, which provides the following steps:

A) causing the O,S-dimethyl dithiocarbonate to react with a primary amine of general formula $R^1NH_2$ in order to obtain an O-methyl thiocarbamate;

B) isomerising the O-methyl thiocarbamate in order to obtain an S-methyl thiocarbamate;

C) causing the S-methyl thiocarbamate with a compound of general formula R'R"NH, wherein R' and R" may be equal or different one in respect of the other and of $R^1$ and may be H, $R^2$ or $R^3$, in order to obtain one of the alkyl-ureas of formula (4), (5) or (6).

23 Claims, No Drawings

PROCESS TO PREPARE ALKYL-UREAS FROM O,S-DIMETHYL DITHIOCARBONATE

FIELD OF THE INVENTION

The present invention relates to a process for the preparation of alkyl-ureas, starting from O,S-dimethyl dithiocarbonate.

BACKGROUND OF THE INVENTION

Alkyl-ureas are a family of well-known compounds. They are important intermediates in the production of isocyanates, drugs, phytomedicines and are used in colouring agents' chemistry, as plasticizers and stabilisers (see Ulmann's Encyclopaedia of Industrial Chemistry, Fifth Edition, 1996, Vol. A27, 355).

There are various processes for preparing monoalkyl-ureas. Among these, the main, long-known processes are the following reactions: i) the reaction of ammonia with a suitable carbamoyle chloride, obtainable by phosgenation of a suitable amine; ii) the reaction of a salt of a suitable amine with a cyanate of an alkaline metal; iii) the reaction of a suitable isocyanate with ammonia; iv) the reaction of a suitable amine with nitro-urea; v) the reaction of transamidation of urea with a suitable amine (see Houben-Weyl, Georg Thieme Verlag, Stuttgart 1952, Vol. VIII, 153). The starting materials used in the first four processes are fairly expensive, highly toxic and/or difficult to obtain. The fifth process does not exhibit the same disadvantages of the first four processes. The transamidation of urea with amines is carried out under pressure in an aqueous or anhydrous medium, as described in DE-C-8 555 551 and in U.S. Pat. No. 3,937,727, or, more easily, in a solvent at atmospheric pressure (see U.S. Pat. No. 4,310,692). The transamidation reaction uses, as a starting material, urea, which is an innocuous, non-toxic and inexpensive compound. However, the yields of the reaction products are fairly limited (they normally reach about 80%) and, at the same time, as results from their physical properties (melting point), their purity is low.

Similarly, the main processes for synthesising di- and tri-alkyl-ureas may be related to the above-described processes for monoalkyl-substituted ureas, i.e.: (i) the reaction of a suitable amine with a suitable carbamoyle chloride, obtainable by phosgenation of a suitable amine; (ii) the reaction of a suitable isocyanate with a suitable amine; (iii) the transamidation reaction of the ureas with suitable amines. The disadvantages of all these processes are the same as those mentioned above, i.e.: as regards the synthetic processes (i) and (ii), the toxicity, difficulty to obtain and/or very high costs of the raw materials; as regards process (iii), the yield and purity problems; on this subject, see for example U.S. Pat. No. 6,281,170, wherein the preparation of N,N,N'-trialkyl-ureas starting from N,N'-dimethyl-urea, with a yield of only 61% is disclosed.

Symmetric and asymmetric N,N'-dialkyl-ureas have been recently prepared also starting from S,S-dimethyl dithiocarbonate (see Man-kiti Leung et al, J. Org. Chem., 1996, 61, 4175). O,S dimethyl dithiocarbonate is an industrially accessible compound (I. Degani, R. Fochi, V. Regondi, Synthesis, 1980, 375 and I. Degani, R. Fochi, V. Regondi, Synthesis, 1980, 149); however, the processes described for its conversion into symmetric and asymmetric N,N'-dialkyl-ureas are not suitable for industrial exploitation, due to the long reaction times, the usually poor yield and, referring in particular to asymmetric ureas, due to the sophisticated operation conditions and the fairly high cost of the reagents.

Concerning symmetric dialkyl-ureas only, it is also possible to synthesise them from carbon dioxide and a suitable monoalkyl-amine at high temperatures and pressures, but with no more than a 75% conversion, which implies the need to recover and purify the gaseous effluents before being able to recycle them in the reaction, as described by U.S. Pat. No. 4,178,309.

SUMMARY OF THE INVENTION

The object of the present invention is a process for preparing mono-, di- and trisubstituted ureas that may solve the disadvantages of the known processes, i.e. a process which may provide high yields of the said ureas, in fair conditions and at a low cost. Such an object is brilliantly solved by the present invention, which relates to a process for preparing alkyl-ureas starting from O,S-dimethyl dithiocarbonate, represented by the following formula (1):

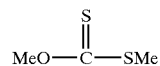

characterised in that is provides the following steps:

A) causing the O,S-dimethyl dithiocarbonate (1) to react with a primary amine of general formula $R^1NH_2$ in order to obtain an O-methyl thiocarbamate of formula (2), wherein $R^1$ is an alkylic, cyclo-alkylic or aryl-alkylic radical

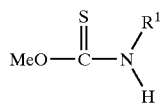

B) isomerising the O-methyl thiocarbamate of formula (2) in order to obtain a S-methyl thiocarbamate of formula (3)

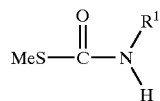

C) causing the S-methyl thiocarbamate of formula (3) to react with a compound of general formula R'R"NH, wherein R' and R" may be equal or different one in respect of the other and may be H, $R^2$ and $R^3$, wherein $R^2$ and $R^3$ are alkylic, cyclo-alkylic or aryl-alkylic radicals and may be equal to or different from $R^1$, in order to obtain one of the alkyl-ureas (4), (5) or (6)

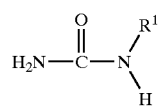

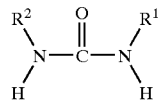

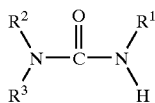

BEST WAY OF CARRYING OUT THE INVENTION

The present invention relates to the preparation of monoalkyl-ureas (4), N,N'-dialkyl-ureas (5) and trialkyl-ureas (6) starting from O,S-dimethyl dithiocarbonate (1), through the intermediate formation of O-methyl thiocarbamates (2) and S-methyl thiocarbamates (3), wherein $R^1$, $R^2$ and $R^3$ represent alkylic, cyclo-alkylic or aryl-alkylic radicals which may be equal or different one in respect of the other and wherein $R^2$ and $R^3$ may also be H.

The first step provides causing the O,S-dimethyl dithiocarbonate (1) to react with a primary amine $R^1NH_2$, wherein an alkylic, cyclo-alkylic or aryl-alkylic radical is bound to the nitrogen atom, which reaction results in yields between 99% and 99.9% of O-methyl thiocarbamate (2), wherein $R^1$ represents the same radicals of the primary amine; the molar ratio $R^1NH_2/(1)$ lies between 1.1 and 1.2; the reaction temperature is between 20° C. and 30° C.; the reaction time is between 2 and 3 hours. The O-methyl thiocarbamate (2) thus obtained is highly pure and may be employed directly in the following step. During the formation of the O-methyl thiocarbamate (2), a mole of methanthiol is produced, which is a product of a certain industrial value and is recovered under the form of sodium salt in aqueous solution, with a 94–98% yield.

The second step consists in isomerising the O-methyl thiocarbamate (2) into S-methyl thiocarbamate (3), wherein $R^1$ represents the same radicals of the primary amine and of the corresponding O-methyl thiocarbamate (2). The isomerisation reaction is made at a temperature between 40° C. and 60° C., in an organic solvent, preferably toluene, in amounts between 0.05 and 4.50 parts in weight per part in weight of (2), using, as initiator, a quantity of dimethyl sulphate between 4% and 8% of the weight of the reagent; the reaction time is between 0.5 and 4 hours; the reaction yields are between 94% and 98%. Dimethyl sulphate may be replaced by a protic organic acid, preferably by methansulphonic acid, used as catalyst. When the reaction is carried out using a protic organic acid, the reaction temperature is about 100° C.; the reaction time is between 2 and 3.5 hours; yields are around 98%. The S-methyl thiocarbamate (3) thus obtained is extremely pure and may be employed directly in the following step.

The third step provides causing the S-methyl thiocarbamate (3), wherein R" represents the same radicals of the primary amine $R^1NH_2$ and of the corresponding O-methyl thiocarbamate (2), to react with a compound of general formula R'R"NH, wherein R' and R" may be equal or different one in respect of the other and they may be H or an alkylic, cyclo-alkylic or aryl-alkylic group. In case a monoalkyl-urea of formula (4) is to be obtained, R'=R"=H and the compound reacting with the S-methyl thiocarbamate is aqueous ammonia. The reaction is carried out at a temperature between 60° C. and 70° C.; the reaction time is between 3 and 6 hours; the reaction yields are between 93% and 96%. The alkyl-urea (4) thus obtained is extremely pure and does not require further purification steps in order to be employed for the intended purposes. During the formation of the monosubstituted urea (4), a mole of methanthiol is produced, which product has—as mentioned before—a good industrial value and which is therefore recovered under the form of sodium salt in aqueous solution, with a 95% yield.

Alternatively, if a dialkyl-urea of formula (5) is to be obtained, R'=H, R"=$R^2$ (which may also correspond to $R^1$) and the compound with which the O-methyl thiocarbamate (3) is made to react is a primary amine $R^2NH_2$. The reaction is carried out at a temperature between 30° C. and 60° C.; the reaction time is between 4 and 8 hours; the reaction yields are between 93% and 96%. The dialkyl-urea (5) thus obtained is extremely pure and may be employed directly for the intended purposes. Also during the formation of the N,N'-disubstituted urea (5), a mole of methanthiol is produced, which is recovered under the form of sodium salt in aqueous solution, with a 95% yield.

Furthermore, if a trialkyl-urea of formula (6) is to be obtained, R'=$R^2$, R"=$R^3$ and the S-methyl thiocarbamate (3) is to react with a secondary amine $R^2R^3NH$. The reaction is carried out at a temperature between 60° C. and 70° C.; the reaction time is between 1 and 2 hours; the reaction yields are between 93% and 96%. The trialkyl-urea (6) thus obtained is extremely pure and may be employed without any further purification for the intended purposes. During the formation of the N,N,N'-trisubstituted urea (6), a mole of methanthiol is produced, which is recovered under the form of sodium salt in aqueous solution, with a 95% yield.

The process constituted by the steps A–C as described above, which employs, as a, starting compound, the O,S-dimethyl dithiocarbonate, an easily accessible, safe and inexpensive compound, provides, in mild and easily obtainable conditions and with usually very high yields, mono-, di- and trialkyl-substituted ureas, respectively of formulae (4), (5) and (6), wherein the substituents $R^1$, $R^2$ and $R^3$, which may be equal or different one in respect of the other, are highly pure and, in most cases, immediately usable alkylic, cyclo-alkylic or aryl-alkylic radicals. The present process also has the important advantage of producing sodium methanthiolate, by completely exploiting the O,S-dimethyl dithiocarbonate (1) used as a starting compound.

The present invention will now be described more in detail, with reference to some examples, which are only provided for purposes of illustration and are not intended to be limiting.

EXAMPLE 1

O,N-Dimethyl Thiocarbamate

A 40% methylamine aqueous solution (g 13.95; moles 0.180) is dropwise added, during 10–15 minutes, into the O,S-dimethyl dithiocarbonate (g 20.00; moles 0.164) placed into a 100 ml flask, while stirring. The mixture temperature is maintained at about 20° C. by means of a refrigerating bath. The reaction is exothermic and produces methanthiol, which is absorbed by a sodium hydroxide aqueous solution. The course of the reaction is monitored through GC and $^1H$ NMR analysis. After 2 hours the reaction is completed. The reaction mixture is then extracted with methylene chloride and the gathered organic extracts are washed in little water, made anhydrous with anhydrous sodium sulphate and made to evaporate by means of a rotating evaporator. The residue is constituted by g 17.21 (99.9% yield) of virtually pure (CG, CG-MS, $^1H$ NMR analysis) O,N-dimethyl thiocarbamate: colourless oil, b.p. 122–123° C./45 mm Hg; MS: m/e 105 ($M^+$); $^1H$ NMR ($CDCl_3$), cis- and trans-rotamers:

δ=2.81 and 3.03 (2d, J=5.12 Hz, 3H, N—CH$_3$), 3.92 and 4.01 (2s, 3H, O—CH$_3$), 6.45 and 7.12 ppm (2 enlarged s, 1H, NH).

EXAMPLE 2

O-Methyl N-Ethyl Thiocarbamate

The process described in example 1 is repeated, with the difference that the 40% methylamine aqueous solution is replaced by 70% ethyleamine aqueous solution (g 12.66; moles 0.197). The reaction is completed in 3 hours. g 19.50 (99.9% yield) of virtually pure (CG, CG-MS, OH NMR analysis) O-methyl N-ethyl thiocarbamate is obtained: colourless oil, b.p. 130–131° C./50 mm Hg; MS: m/e 119 (M$^+$); $^1$H NMR (CDCl$_3$), cis- and trans-rotamers: δ=1.10 and 1.18 (2t, J=8.00 Hz, 3H, CH$_2$—$\underline{CH}_3$), 3.02–3.72 (m, 2H, CH$_2$), 3.90 and 4.00 (2s, 3H, O—CH$_3$), 6.82 and 7.50 ppm (2 enlarged s, 1H, NH).

EXAMPLE 3

O-Methyl N-Butyl Thiocarbamate

The process described in example 1 is repeated, with the difference that the 40% methylamine aqueous solution is replaced by butylamine (9 14.38; moles 0.197). The reaction is completed in 3 hours. g 23.89 (99.1% yield) of virtually pure (CG, CG-MS, $^1$H NMR analysis) O-methyl N-butyl thiocarbamate is obtained: colourless oil, b.p. 118–120° C./65 mm Hg; MS: m/e 147 (M$^+$); $^1$H NMR (CDCl$_3$), cis- and trans-rotamers: δ=0.85 (q, J=7.48 Hz, 3H, CH$_2$—$\underline{CH}_3$), 1.21–1.35 and 1.39–1.55 (2 m, 4H, CH$_2$—$(\underline{CH}_2)_2$—CH$_3$), 3.19 and 3.46 (2td, J=7.16, 2H, N—CH,), 3.89 and 3.98 (2s, 3H, O—CH$_3$), 6.45 and 7.23 ppm (2 enlarged s, 1H, NH).

EXAMPLE 4

O-Methyl N-Cyclohexil Thiocarbamate

The process described in example 1 is repeated, with the difference that the 40% methylamine aqueous solution is replaced by cyclohexilamine (g 19.50; moles 0.197). The reaction is completed in 4.5 hours. g 28.34 (99.9% yield) of virtually pure (CG, CG-MS, $^1$H NMR analysis) O-methyl N-cyclohexil thiocarbamate is obtained: crystallised from pentane, it has m.p. 39–40° C.; MS: m/e 173 (M$^+$); $^1$H NMR (CDCl$_3$), cis- and trans-rotamers: δ=0.92–1.30, 1.37–1.65 and 1.65–1.95 (3m, 5:3:2, 10H, 5CH$_2$), 3.45–3.55 (m, 1H, CH), 3.78 and 3.88 (2s, 3H, O—CH$_3$), 6.43 and 7.30 ppm (2 enlarged s, 1H, NH).

EXAMPLE 5

O-Methyl N-Benzyl Thiocarbamate

The process described in example 1 is repeated, with the difference that the 40% methylamine aqueous solution is replaced by benzylamine (g 19.26; moles 0.180). The reaction is completed in 3.5 hours. g 29.38 (99% yield) of virtually pure (CG, CG-MS, $^1$H NMR analysis) O-methyl N-benzyl thiocarbamate is obtained: crystallised from petroleum ether, it has m.p. 45.6–46.10° C.; MS: m/e 181 (M$^+$); $^1$H NMR (CDCl$_3$), cis- and trans-rotamers: δ=4.00 and 4.07 (2s, 3H, O—CH$_3$), 4.41 and 4.73 (2d, J=5.00 and 6.00 Hz, 2H, N—CH$_2$), 6.56 ppm (enlarged s, 1H, NH), 7.19–7.45 (m, 5H, phenyl).

EXAMPLE 6

N,S-Dimethyl Thiocarbamate

A quantity of toluene and dimethyl sulphate, each of which equal to 56 of the thiocarbamate weight (g 0.84), is added to the O,S dimethyl thiocarbamate (g 16.80, moles 0.16). The mixture is heated to 50° C. by means of an oil bath, while stirring. The course of the reaction is monitored through GC and $^1$H NMR analysis. After 2.5 hours the reaction is completed. After cooling the mixture to room temperature, it is neutralised with 30% aqueous ammonia and the stirring is maintained for 10–15 minutes. The reaction mixture is then extracted with methylene chloride and the gathered organic extracts are washed in little water, anhydrated with anhydrous sodium sulphate and made to evaporate by means of a rotating evaporator. The residue is g 15.96 (95% yield) of virtually pure (CG, CG-MS, $^1$H NMR analysis) N,S-dimethyl thiocarbamate: colourless oil, b.p. 81–82° C./45 mm Hg; MS: m/e 105 (M$^+$); $^1$H NMR (CDCl$_3$): δ=2.31 (s, 3H, S—CH$_3$), 2.84 (d, J=4.76 Hz, 3H, N—CH$_3$), 5.65 ppm (enlarged s, 1H, NH).

EXAMPLE 7

S-Methyl N-Ethyl Thiocarbamate

The process described in example 6 is repeated, with the difference that the O,S dimethyl thiocarbamate is replaced by an equal quantity of O-methyl N-ethyl thiocarbamate (g 19.04; moles 0.16). The reaction is completed in 4 hours at 40° C. g 18.22 (95.7% yield) of virtually pure (CG, CG-MS, $^1$H NMR analysis) S-methyl N-ethyl thiocarbamate is obtained: colourless oil, b.p. 82–84° C./50 mm Hg; MS: m/e 119 (M$^+$); $^1$H NMR (CDCl$_3$): δ=1.20 (t, J=6.40 Hz, 3H, CH$_2$—$\underline{CH}_3$), 2.36 (s, 3H, S—CH$_3$), 3.35 (dq, J=6.00 Hz, 2H, CH$_2$), 6.32 ppm (enlarged s, 1H, NH).

EXAMPLE 8

S-Methyl N-Ethyl Thiocarbamate

A quantity of anhydrous methansulphonic acid equal to 5% of the thiocarbamate weight (g 0.95) is added to the S-methyl N-ethyl thiocarbamate (g 19.04, moles 0.16), while stirring. The mixture is then heated to 100° C. by means of an oil bath. The course of the reaction, which is completed in 2 hours, is monitored through GC and $^1$H NMR analysis. After cooling the mixture to room temperature, it is extracted with methylene chloride and the gathered organic extracts are washed in little water, anhydrated with anhydrous sodium sulphate and made to evaporate by means of a rotating evaporator. The residue is g 18.61 (97.7% yield) of virtually pure (CG, CG-MS, $^1$H NMR analysis) S-methyl N-ethyl thiocarbamate. The spectroscopic characteristics thereof are identical to those of the product obtained in example 7.

EXAMPLE 9

S-Methyl N-Butyl Thiocarbamate

The process described in example 6 is repeated, with the difference that the O,S-dimethyl thiocarbamate is replaced by an equal quantity of O-methyl N-butyl thiocarbamate (g 23.52; moles 0.16). The reaction is completed in 4 hours at 50° C. g 22.10 (94% yield) of virtually pure (CG, CG-MS, $^1$H NMR analysis) S-methyl N-butyl thiocarbamate is obtained: crystallised from pentane, it has m.p. 34.8–35.4° C.; MS: m/e 147 (M$^+$); $^1$H NMR (CDCl$_3$): δ=0.80–1.10 (m, 3H, CH$_2$—$\underline{CH}_3$), 1.20–1.70 (m, 4H, CH$_2$—$(\underline{CH}_2)_2$—CH$_3$), 2.35 (s, 3H, S—CH$_3$), 3.05–3.45 (m, 2H, N—CH$_2$), 6.18 ppm (enlarged s, 1H, NH).

EXAMPLE 10

S-Methyl N-Cyclohexyl Thiocarbamate

The process described in example 6 is repeated, with the difference that the O,S dimethyl thiocarbamate is replaced by an equal quantity of O-methyl N-cyclohexil thiocarbamate (g 27.68; moles 0.16). The reaction is completed in 30 minutes at 60° C. g 26.99 (97.5% yield) of virtually pure (CG, CG-MS, $^1$H NMR analysis) S-methyl N-cyclohexil thiocarbamate is obtained: crystallised from petroleum ether-ethanol, it has m.p. 111–111.3° C.; MS: m/e 173 (M$^+$); $^1$H NMR (CDCl$_3$): δ=0.96–2.09 (m, 10H, 5 CH$_2$), 2.31 (s, 3H, SCH$_3$), 3.39–3.99 (m, 1H, CH), 5.52 ppm (enlarged s, 1H, NH).

EXAMPLE 11

S-Methyl N-Cyclohexil Thiocarbamate

The process described in example 8 is repeated, with the difference that the S-methyl N-ethyl thiocarbamate is replaced by an equal quantity of O-methyl N-cyclohexil thiocarbamate (g 27.68; moles 0.16). The reaction is completed in 3.5 hours at 100° C. g 27.29 (98.6% yield) of virtually pure (CG, CG-MS, $^1$H NMR analysis) S-methyl N-cyclohexil thiocarbamate is obtained. The spectroscopic characteristics thereof are identical to those of the product obtained in example 11.

EXAMPLE 12

S-Methyl N-Benzyl Thiocarbamate

The process described in example 6 is repeated, with the difference that the O,S dimethyl thiocarbamate is replaced by an equal quantity of O-methyl N-benzyl thiocarbamate (g 28.96; moles 0.16). The reaction is completed in 60 minutes at 50° C. g 28.38 (98% yield) of virtually pure (CG, CG-MS, $^1$H NMR analysis) S-methyl N-benzyl thiocarbamate is obtained: crystallised from ethanol, it has m.p. 75.7–76.7° C.; MS: m/e 181 (M$^+$); $^1$H NMR (CDCl$_3$): δ=2.35 (s, 3H, S—CH$_3$), 4.45 (d, J=6.0 Hz, 2H, N—CH$_2$), 5.90 ppm (enlarged s, 1H, NH), 7.22–7.39 (m, 5H, phenyl).

EXAMPLE 13

Methyl Urea

A quantity of 30% aqueous ammonia (g 102, moles 1.80) is added, while stirring, to the N,S-dimethyl thiocarbamate (g 15.75, moles 0.15) and the mixture is heated to 65° C., still stirring it. The reaction produces methanthiol, which is absorbed by a sodium hydroxide aqueous solution. The course of the reaction is monitored through thin layer chromatography (SiO$_2$; eluent: CHCl$_3$/CH$_3$OH, 9.8:0.2). The reaction is completed in 3 hours. The water is distilled by means of a rotating evaporator, the solid product is then completely dried by adding chloroform and subsequently distilling it. g 10.99 of product is obtained, which is 97% pure. After washing the raw residue at 0° C. in 4–5 ml of anhydrous dioxane, g 10.66 (yield 96%) of pure (TLC, GC, GC-MS, $^1$H NMR) methyl urea is obtained: m.p. 101.9–102.1° C.; MS: m/e 74; $^1$H NMR (DMSO-d$_6$): δ=2.46 (d, J=5.00 Hz, 3H, CH$_3$), 5.49 (enlarged s, 2H, NH$_2$), 5.85 ppm (enlarged s, 1H, NH).

EXAMPLE 14

Ethyl Urea

The process described in example 13 is repeated, with the difference that the N,S dimethyl thiocarbamate is replaced by an equal quantity of S-methyl N-ethyl thiocarbamate (g 17.85; moles 0.15) and that the 30% ammonia aqueous solution is g 127.5 (moles 2.25). The reaction is completed in 6 hours at 70° C. g 12.54 of 98% pure, solid product is obtained. From the raw residue, after washing it at 0° C. in 4–5 ml ethyl acetate, g 12.28 (yield 93%) of pure (TLC, GC, GC-MS, $^1$H NMR) ethyl urea is obtained: m.p. 93.3° C.; MS: m/e 88; $^1$H NMR (CDCl$_3$3): δ=1.16 (t, J=7.00 Hz, 3H, CH$_3$), 3.20 (dq, J=7.00, 2H, N—CH$_2$), 5.01 (enlarged s, 2H, NH$_2$), 5.55 ppm (enlarged s, 1H, NH).

EXAMPLE 15

Butyl Urea

The process described in example 13 is repeated, with the difference that the N,S-dimethyl thiocarbamate is replaced by an equal quantity of S-methyl N-butyl thiocarbamate (g 22.05; moles 0.15). The 30% ammonia aqueous solution is g 102 (moles 1.80). The reaction is completed in 4 hours at 70° C. g 17.23 of 96% pure, solid product is obtained. From the raw residue, after washing it at 0° C. in 4–5 ml ethyl acetate, g 16.53 (yield 95%) of pure (TLC, GC, GC-MS, $^1$H NMR) butyl urea is obtained: m.p. 96.8° C.; MS: m/e 116; $^1$H NMR (CDCl$_3$): δ=0.75–1.15 (m, 3H, CH$_2$—CH$_3$), 1.20–1.72 (m, 4H, CH$_2$—(CH$_2$)$_2$—CH$_3$), 2.96–3.38 (m, 2H, N—CH$_2$), 5.00 (enlarged s, 2H, NH$_2$), 5.75 ppm (enlarged s, 1H, NH).

EXAMPLE 16

Cyclohexil Urea

The process described in example 13 is repeated, with the difference that the N,S dimethyl thiocarbamate is replaced by an equal quantity of S-methyl N-cyclohexil thiocarbamate (g 25.95; moles 0.15) and that the 30% ammonia aqueous solution is g 76.5 (moles 1.35). In this example, about 3 g per g of thiocarbamate (ml 78) ethylic alcohol is also added. The reaction is completed in 6 hours at 70° C. g 20.66 of pure (TLC, GC, GC-MS, $^1$H NMR) cyclohexil urea is obtained: m.p. 193.8–194.5° C.; MS: m/e 142; $^1$H NMR (DMSO-d$_6$): δ=0.51–0.70, 0.70–0.83, 0.99–1.08, 1.10–1.20 and 1.20–1.30 (5m, 3:2:1:2:2, 10H, 5CH$_2$), 2.75–2.89 (m, 1H, CH), 4.88 (enlarged s, 2H, NH$_2$), 5.39 ppm (d, J=7.88 Hz, 1H, NH).

EXAMPLE 17

Benzyl Urea

The process described in example 13 is repeated, with the difference that the N,S-dimethyl thiocarbamate is replaced by an equal quantity of S-methyl N-benzyl thiocarbamate (g 27.15; moles 0.15) and that the 30% ammonia aqueous solution is g 76.5 (moles 1.35). In this example, as in example 16, about 3 g per g of thiocarbamate (ml 81) ethylic alcohol or dioxane, alternatively, is also added. The reaction is completed in 6 hours at 60° C. g 22.05 of 97% pure solid product is obtained. From the raw residue, after washing it at room temperature in toluene (50–60 ml), g 21.38 (yield 95%) of pure (TLC, GC, GC-MS, $^1$H NMR) benzyl urea is obtained: m.p. 149° C.; MS: m/e 150; $^1$H NMR (DMSO-d$_3$): δ=4.15 (d, J=6.00 Hz, 2H, CH$_2$), 5.42 (enlarged s, 2H, NH$_2$), 6.35 (enlarged s, 1H, NH), 7.05–7.25 ppm (m, 5H, phenyl).

EXAMPLE 18

N-Ethyl-N'methyl Urea

The reaction mixture constituted by N-ethyl, S-methyl thiocarbamate (g 8.45, moles 0.071) and methylamine (g 6.6, moles 0.213; g 16.5 of 40% aqueous solution) is continuously stirred and heated to 50–55° C. The freed methanthiol is absorbed by a sodium hydroxide aqueous solution. GC monitoring shows that the reaction is completed in 1 hour. The methanthiol is completely removed from the reaction mixture through an air flow. The methylamine that is still present and the water are removed by means of a rotating evaporator, with the possible help of an azeotrope-producing solvent. g 7.24 (quantitative yield) of virtually pure (TLC, GC, GC-MS verified) N-ethyl-N-methyl urea is produced; after drying it with chloroform and subsequently crystallising it from ethylic ether, it has m.p. 50.5–51.0° C.; MS: m/e 102 (M$^+$); $^1$H NMR (CDCl$_3$), d=1.12 (t, J=7.00 Hz, 3H, CH$_2$—C$\underline{H}_3$), 2.75 (d, J=5.00 Hz, 3H, NH—C$\underline{H}_3$), 3.17 (dq, J=7.00 Hz, 2H, CH$_2$), 5.53 (enlarged s, 1H, NH).

EXAMPLE 19

N,N'-Diethyl Urea

The reaction mixture constituted by N-ethyl, S-methyl thiocarbamate (g 4.6, moles 0.039) and ethylamine (g 3.8, moles 0.086; g 5.53 of 70% aqueous solution) is continuously stirred and heated to 40° C. The freed methanthiol is absorbed by a sodium hydroxide aqueous solution. The process continues until the starting thiocarbamate is over (chromatographic analyses: about 8 hours). The methanthiol is completely removed from the reaction mixture through an air flow. The methylamine that is still present and the water are removed by means of a rotating evaporator, possibly with the help of an azeotrope-producing solvent. g 4.52 (quantitative yield) of virtually pure (TLC, GC, GC-MS) N,N'-diethyl urea is produced; after drying it with chloroform and crystallising it from toluene, it has m.p. 111–1120° C.; MS: m/e 116 (M$^+$); $^1$H NMR (CDCl$_3$), d=1.05 (t, J=7.00 Hz, 6H, 2 C$\underline{H}_3$), 3.09 (dq, J=7.00 Hz, 4H, 2 C$\underline{H}_2$), 5.40 ppm (enlarged s, 2H, 2NH).

EXAMPLE 20

N,N-Dibutyl-N'methyl Urea

The reaction mixture constituted by N,S-dimethyl thiocarbamate (g 15.75, moles 0.15) and dibutylamine (g 23.22, moles 0.18) is continuously stirred and heated to 65–70° C. The reaction produces methanthiol, which is absorbed by a sodium hydroxide aqueous solution. The course of the reaction is monitored through GC and MS analysis. The reaction is completed in 2 hours. The dibutylamine in excess is removed through distillation by means of a rotating evaporator. g 26.51 (95% yield) of virtually pure (TLC, GC, GC-MS) N,N-dibutyl-N'methyl urea is produced: crystallised from pentane it has m.p. 46.0–46.20° C.; MS: m/e 185 (M$^+$); $^1$H NMR (CDCl$_3$), d=0.98 (t, J=6.00 Hz, 6H, 2 CH$_2$—C$\underline{H}$3), 1.12–1.75 (m, 8H, CH$_2$—(C$\underline{H}_2$)$_2$CH$_3$), 2.84 (d, J=5.00 Hz, 3H, NH—C$\underline{H}_3$), 3.20 (t, J=7.20 Hz, 4H N[CH$_2$—(C$\underline{H}_2$)$_2$CH$_3$)$_2$), 4.35 ppm (enlarged s, 1H, NH).

EXAMPLE 21

Ethyl Urea

1$^{st}$ step—A 500 ml flask is arranged, provided with a bottom discharge, mechanical stirrer, dripping funnel with pressure compensator, reflux refrigerant connected to a tube drawing from a 12.8% sodium hydroxide aqueous solution (g. 512.5) contained into a first trap, which in turn is connected to a trapping system comprising a series of traps, a sodium hydroxide one, a diluted sulphuric acid one, a hypochlorite one and an active carbons one. g 200 (moles 1.64) of O,S-dimethyl dithiocarbonate is placed into the flask, which kept under a weak nitrogen flow and, while mechanically stirring, g 144.5 of 61.3% (moles 1.97) ethylamine is poured at such a speed that the maximum reaction temperature does not exceed 45° C. (about 1 hour). The mass is then conditioned to 50–55° C. for 1 hour at atmospheric pressure and then for a further hour at reduced pressure (400 mm Hg ca.). The mass is brought back to ordinary temperature and pressure, g 50 of water is added and the stirring is stopped; as a lower phase, g 193.1 (yield 98.9%) of O-methyl N-ethyl thiocarbamate, under the form of colourless oil, is separated.

The aqueous solution of the first sodium hydroxide trap contains g 108.65 (yield 94%) of sodium methanthiolate.

2$^{nd}$ step—g 193.1 of O-methyl N-ethyl thiocarbamate obtained in the 1$^{st}$ step is introduced into a 2000 ml flask, provided with a distillation head connected to a condenser and to a collector, and diluted with g 1120 of toluene. The solution is made anhydrous through distillation with the azeotrope water/toluene. After the distillation, the residual solution (g 1051.6) is brought to 45° C. and the distillation head is replaced with a reflux refrigerant. Then, while mechanically stirring, g 9.6 of dimethyl sulphate is added at such a speed that the maximum reaction temperature does not exceed 47° C. The mass is conditioned to 45° C. for 4 hours and then cooled to room temperature. g 8.6 of a 30% ammonium hydroxide aqueous solution is added, the mixture is stirred for 30 minutes and the organic phase is separated. The aqueous phase is deeply extracted with toluene. The organic extracts are gathered, washed in little water and dried. After the distillation with toluene, g 196 of 96.5% S-methyl N-ethyl thiocarbamate is obtained.

3$^{rd}$ step—A 1000 ml flask, provided with mechanical stirrer, dripping funnel with pressure compensator, reflux refrigerant connected to a trap system equal to that described in the 1$^{st}$ step is arranged. Under a weak nitrogen flow, g 196 of raw S-methyl N-ethyl thiocarbamate obtained in the 2$^{nd}$ step is placed inside and, while stirring, g 762 of a 30% aqueous ammonia solution (9 eq.) is added. The mixture is heated to 60° C. and the reaction is continued for 4 hours. The reflux refrigerant is replaced by a distillation head connected to a condenser and a collector, which collector is in turn connected to the trap system. g 237 of water is distilled. g 389 of 33.2% ethyl urea aqueous solution is obtained, the dry residue of which being 98.5% pure (GC area %). The aqueous solution of the first sodium hydroxide trap contains g 109.8 (yield 95%) of sodium methanthiolate. The sulphuric acid trap trapped g 202 of ammonia (i.e. 99% of the non-reacted part).

What is claimed is:

1. A process for preparing alkyl-ureas, starting from O,S-dimethyl dithiocarbonate, having the following formula (1):

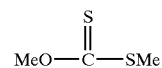

comprising the following steps:

A) reacting O,S-dimethyl dithiocarbonate (1) with a primary amine of formula R$^1$NH$_2$, where R$^1$ is alkyl, cycloalkylic or arylalkyl, so as to obtain an O-methyl thiocarbamate of formula (2):

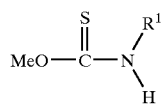

B) isomerising the O-methyl thiocarbamate of formula (2), so as to obtain an S-methyl thiocarbamate of formula (3):

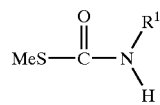

C) reacting the S-methyl thiocarbamate of formula (3) with a compound of formula R'R"NH, where R' and R" are H, $R^2$ or $R^3$, where $R^2$ and $R^3$ are alkyl, cycloalkyl or arylalkyl and can be the same or different and can be the same as or different from $R^1$, so as to obtain one of the alkyl-ureas (4), (5) or (6):

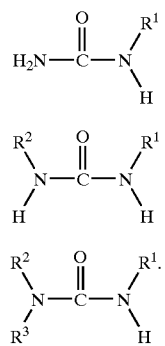

2. A process as in claim 1, wherein, in step A), the molar ratio $R^1NH_2$/dithiocarbonate of formula (1) is between 1.1 and 1.2.

3. A process as in claim 1, wherein the reaction temperature of step A) is between 20° C. and 30° C.

4. A process as in claim 1, wherein the reaction time for step A) is between 2 and 3 hours.

5. A process as in claim 1, wherein the temperature of step B) is between 40° C. and 60° C.

6. A process as in claim 1, wherein step B) is carried out in an organic solvent.

7. A process as in claim 6, wherein said organic solvent is toluene.

8. A process as in claim 6, wherein said organic solvent is present in amounts between 0.05 and 4.50 parts by weight per part by weight of said O-methyl thiocarbamate of formula (2).

9. A process as in claim 1, using dimethyl-sulphate as an initiator in step B) in an amount between 4% and 8% by weight of the weight of the O-methyl thiocarbamate of formula (2).

10. A process as in claim 1, wherein the reaction time for step B) is between 0.5 and 4 hours.

11. A process as in claim 1, and using a protic organic acid as an initiatior for step B).

12. A process as in claim 11, wherein said acid is methanesulphonic acid.

13. A process as in claim 12, wherein the reaction temperature of step B) is about 100° C.

14. A process as in claim 11, wherein the reaction time is between 0.5 and 1 hour.

15. A process as in claim 1, wherein, in step C), R'=R"=H, and the compound reacting with S-methyl thiocarbamate is aqueous ammonia.

16. A process as in claim 15, wherein the reaction temperature of step C) is between 60° C. and 70° C.

17. A process as in claim 15, wherein the reaction time for step C) is between 3 and 6 hours.

18. A process as in claim 1, wherein, in step C), R'=H, R"=$R^2$, and the compound reacting with S-methyl thiocarbamate of formula (3) is a primary aliphatic amine $R^2NH_2$.

19. A process as in claim 18, wherein the reaction temperature of step C) is between 30° C. and 60° C.

20. A process as in claim 18, wherein the reaction time is between 4 and 8 hours.

21. A process as in claim 1, wherein, in step C), R'=$R^2$, R"=$R^3$, and reacting the S-methyl thiocarbamate of formula (3) with a secondary aliphatic amine $R^2R^3NH$.

22. A process as in claim 21, wherein the reaction temperature of step C) is between 60° C. and 70° C.

23. A process as in claim 21, wherein the reaction time for step C) is between 1 and 2 hours.

* * * * *

UNITED STATES PATENT AND TRADEMARK OFFICE
CERTIFICATE OF CORRECTION

PATENT NO. : 6,723,875 B1  
DATED : April 20, 2004  
INVENTOR(S) : Edoardo Pallucca et al.

Page 1 of 1

It is certified that error appears in the above-identified patent and that said Letters Patent is hereby corrected as shown below:

<u>Title page,</u>
Insert item as follows:
-- [30]     Foreign Application Priority Data,
Feb. 07, 2002  (IT).....................MI2002A000227 --.

Signed and Sealed this

Third Day of August, 2004

JON W. DUDAS
*Acting Director of the United States Patent and Trademark Office*